United States Patent
Bennett et al.

(10) Patent No.: US 7,033,181 B1
(45) Date of Patent: Apr. 25, 2006

(54) BRIEF THERAPY TREATMENT DEVICE AND METHOD

(76) Inventors: Richard W. Bennett, 8716 Pine Ave., Gary, IN (US) 46403; Patricia W. Bennett, 8716 Pine Ave., Gary, IN (US) 46403

( * ) Notice: Subject to any disclaimer, the term of this patent is extended or adjusted under 35 U.S.C. 154(b) by 1160 days.

(21) Appl. No.: 09/877,741

(22) Filed: Jun. 11, 2001

Related U.S. Application Data

(60) Provisional application No. 60/212,732, filed on Jun. 20, 2000.

(51) Int. Cl.
*G09B 19/00* (2006.01)

(52) U.S. Cl. ...................................... 434/236

(58) Field of Classification Search ............... 434/236, 434/237, 238, 433; 273/299, 300, 302
See application file for complete search history.

(56) References Cited

U.S. PATENT DOCUMENTS

| | | | | |
|---|---|---|---|---|
| 4,216,594 A | * | 8/1980 | Farley et al. | 434/236 |
| 5,405,266 A | * | 4/1995 | Frank et al. | 434/237 |
| 5,580,254 A | * | 12/1996 | Ramsey | 434/236 |
| 5,702,253 A | * | 12/1997 | Bryce et al. | 434/236 |
| 5,741,137 A | * | 4/1998 | Aduvala | 434/236 |
| 6,422,558 B1 | * | 7/2002 | Chambers | 273/146 |

* cited by examiner

*Primary Examiner*—Kurt Fernstrom
(74) *Attorney, Agent, or Firm*—Tipton L. Randall

(57) ABSTRACT

The present invention is directed to a device for interactive psycho/social evaluation and treatment of individuals, and to a method of using the device in the evaluation and treatment of individuals. The client is asked to distribute, under specific headings, 31 adjective words that describe their behavior. This distribution, along with some internal test manipulation not only pictures their behavior but their defense mechanisms, as well. As the client describes the reasons for the distribution of adjective words, important psycho/social historical information is also obtained.

11 Claims, 2 Drawing Sheets

BRIEF THERAPY TREATMENT DEVICE AND METHOD

CROSS-REFERENCE TO RELATED APPLICATIONS, IF ANY

This application claims the benefits under 35 U.S.C. §119(e) of co-pending provisional application Ser. No. 60/212,732, filed 20 Jun., 2000. Application Ser. No. 60/212,732 is hereby incorporated by reference.

STATEMENT REGARDING FEDERALLY SPONSORED RESEARCH OR DEVELOPMENT

Not applicable. REFERENCE TO A MICROFICHE APPENDIX, IF ANY
Not applicable.

BACKGROUND OF THE INVENTION

1. Field of the Invention

The present invention relates to a device for interactive psycho/social evaluation and treatment of individuals and families, and to a method of using the device in the evaluation and treatment of individuals and families.

2. Background Information

The first step in the development of the invention was the awareness of a need for an interactive psycho/social measurement tool that both helps evaluate Attention Deficit Hyperactivity Disorder (ADHD) adults and plans treatment strategies that effectively reverses the anxiety, depression, hyper activity, inattention and acting out behavior usually associated with this disorder. Previously, there was no interactive psycho/social tool useful in the determination of ADHD, and according to some authors, the external rating scales that were used for evaluation contributed to the problem, rather than helped solve it. The present invention is suitable for interactive psycho/social evaluation and treatment of ADHD adults and others suffering from various psycho/social disorders.

As the development of this instrument continued, it became obvious that it had other uses, as well. Since the instrument helps the client see the ambiguities of his emotional defense patterns, as well as the behaviors that are developed to cope with those defenses, the instrument may be used with anyone who can read and understand the concepts. New adjectives (adjective cards) were added, and now the instrument is used as an interactive psycho/social tool with anyone of the appropriate skill level. It is particularly useful in understanding and predicting violence in all categories of individuals.

SUMMARY OF THE INVENTION

The present invention is directed to a device for interactive psycho/social evaluation and treatment of individuals, and to a method of using the device in the evaluation and treatment of individuals. The present invention is exemplified in a number of implementations and applications, some of which are summarized below.

According to an example embodiment, the present invention includes a psycho/social evaluative instrument based completely upon how the client describes his behavior. The client is asked to distribute, under specific headings, 31 adjective words that describe his behavior. This distribution, along with some internal test manipulation not only pictures their behavior but their defense mechanisms, as well. As the client describes the reasons for the distribution of adjective words, important psycho/social historical information is also obtained.

This test method is a cooperative instrument between client and therapist. The client actually makes his own behavioral diagnosis and treatment plan. It is cooperative with other testing and is an important part of a total psycho/social evaluation. It is cooperative with other disciplines and is helpful to school professionals, medical professionals and family. Having accurate behavioral information leads to a much easier and more correct DSM-IV diagnosis.

Because this instrument asks clients to present their behavior, the presenting problem becomes glaringly obvious. This evaluation instrument lets the client interact with himself/herself in devising a workable treatment plan. Thus, it saves both time and money.

The instrument, because it describes behaviors, serves as a risk predictor. It describes actual behaviors and the client's attitude toward those behaviors. It presents historical information as to when those behaviors developed, and provides information on the client's attitudes about violence. This becomes a very important risk predictor, when combined with actual behaviors and attitudes about them. The material is presented in clear, easy to understand, non-psychological jargon.

The above summary of the present invention is not intended to describe each illustrated embodiment or every implementation of the present invention. The detailed descriptions that follow more particularly exemplify these embodiments.

DESCRIPTION OF THE EMBODIMENTS

Figure 1:
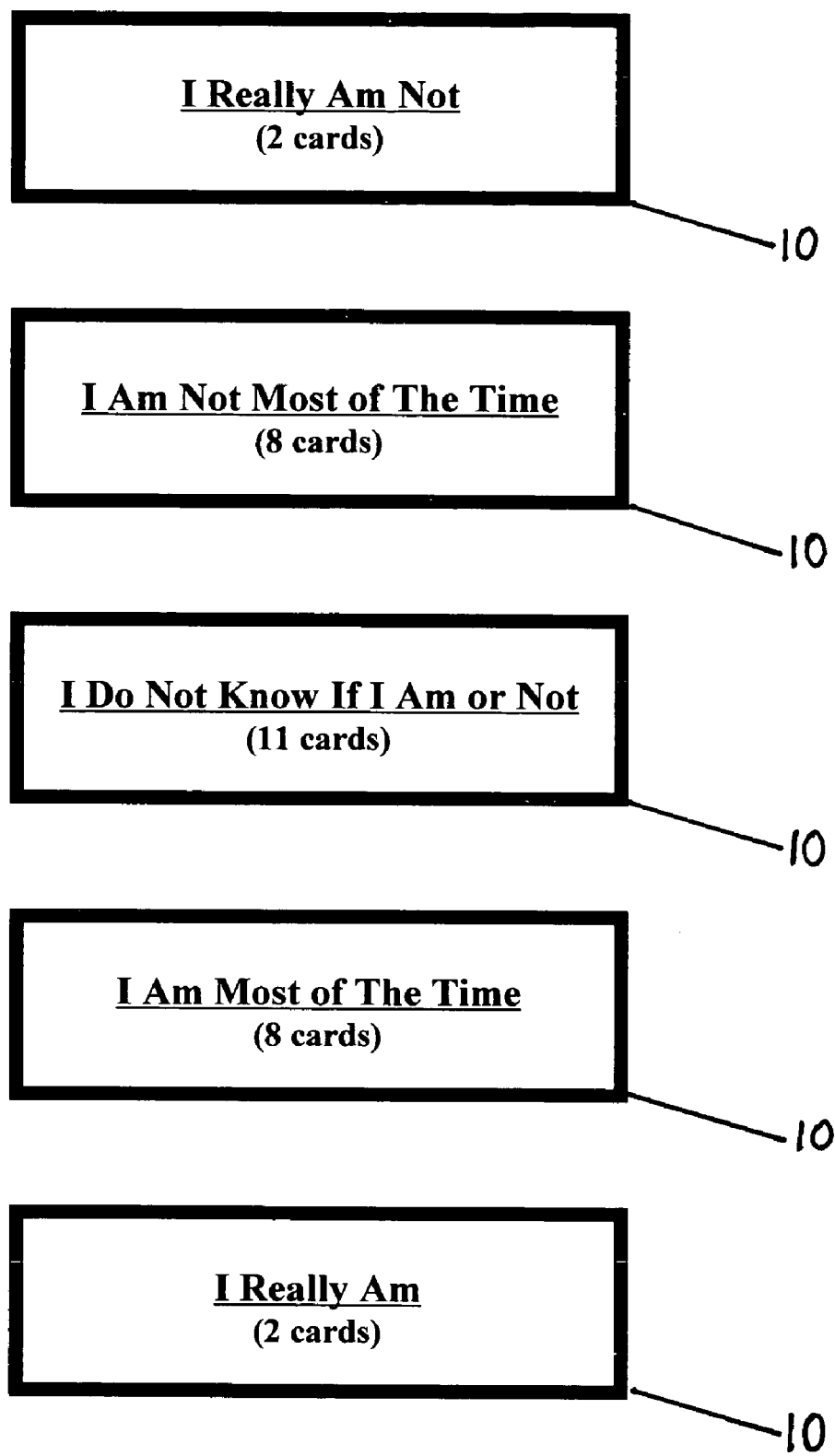
FIG. 1 shows the five heading cards employed in one embodiment of the present invention.
Figure 2:
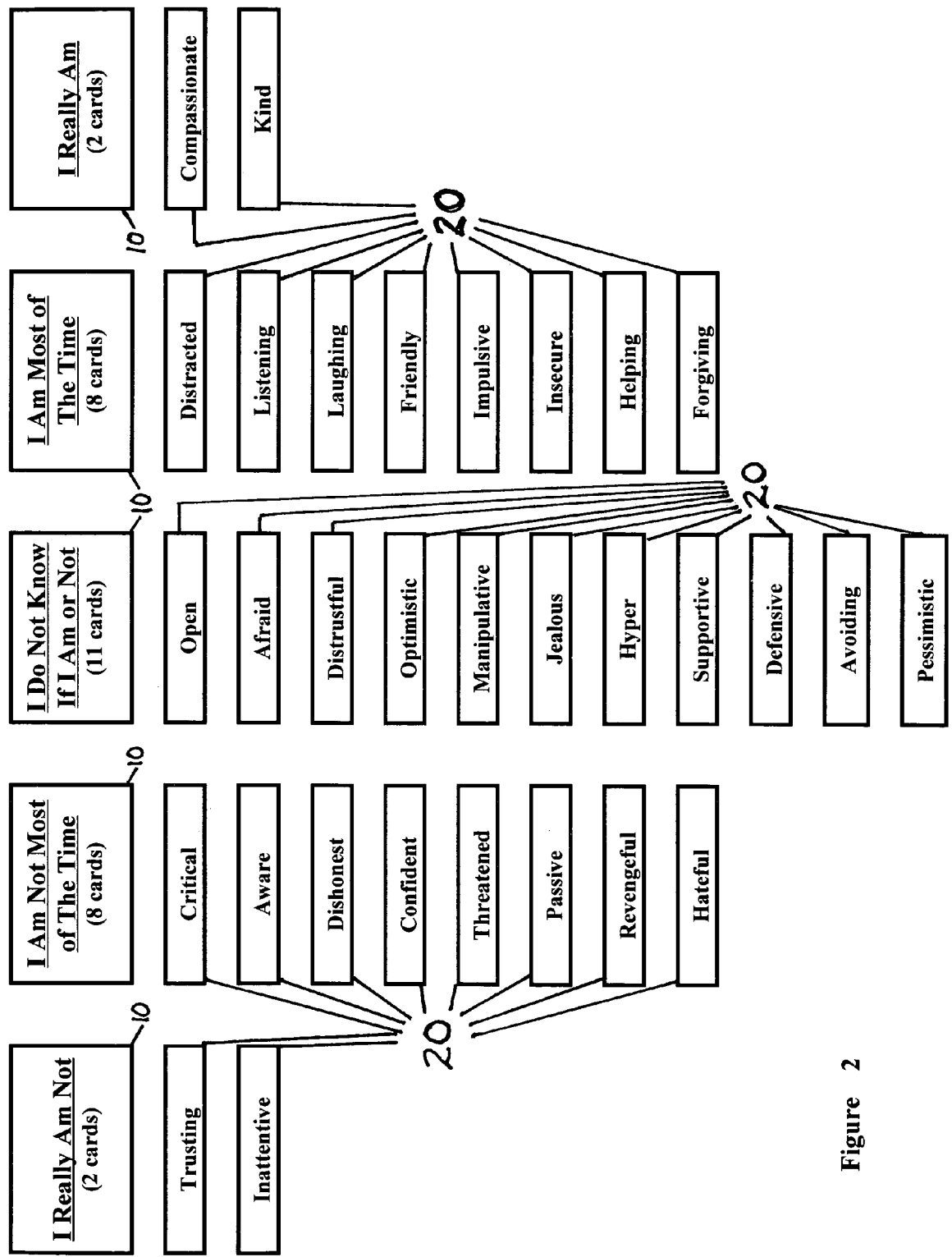
FIG. 2 shows an example layout of the five heading cards and the thirty-one adjective cards employed in one embodiment of the present invention.

The present invention is believed to be applicable to a device for interactive psycho/social evaluation and treatment of individuals, and to a method of using the device in the evaluation and treatment of individuals. While the present invention is not limited to such evaluation and treatment, an appreciation of various aspects of the invention is best gained through a discussion of various examples using this application.

As indicated above, the individual client is asked to distribute under five specific headings, thirty-one adjective words that describe his behavior. The headings and adjective 5 words may be presented to the individual in any suitable form, such as on cards or similar printed medium, or on a computer or video screen. The basic requirement is that the individual be able to distribute/move the adjective words within/between the specific headings. The present invention is described in the context of using printed heading cards and adjective word cards, but other representations of the described headings and adjective words may be employed with comparable results.

According to a particular embodiment, the present invention includes a set of cards having a first subset and a second subset. The first subset contains five (5) cards 10 each having one of the phrases: (1) "I Really Am Not {2} ". (2) "I Am Not Most of the Time {8} ". (3) "I Do Not Know If I Am or Not {11} ". (4) "I Am Most of the Time {8} ". (5) "I Really Am {2} ". The second subset contains thirty-one (31) cards 20 each having one of the words: (A) Listening. (B) Confident. (C) Trusting. (D) Open. (E) Laughing. (F) Kind. (G) Supportive. (H) Friendly. (I) Aware. (J) Compassionate. (K) Forgiving. (L) Helping. (M) Optimistic. (N) Passive. (0) Distrustful. (P) Avoiding. (Q) Insecure. (R) Dishonest. (S) Manipulative. (T) Defensive. (U) Afraid. (V) Threatened. (W) Jealous. (X) Critical. (Y) Hateful. (Z) Revengeful. (AA) Pessimistic. (BB) Inattentive. (CC) Distracted. (DD) Hyper. (EE) Impulsive.

The method of using the above-described two subsets of cards will be referred to as the Brief Therapy Treatment Planner method, or simply "BTTPlanner".

Evaluative, potential treatment, and behavioral data received during the administration of the BTTPLANNER, is presented in an interactive, psycho/social format. The interpretation of the behavioral material is similar in content to the interpretation of emotional information acquired during the administration of projective testing instruments.

This is much different than material received from a checklist (True/False) or cookbook-type diagnostic instrument. It is easy to compare diagnostic data from a checklist against DSM-IV criteria. It is, however, on a checklist or cookbook instrument, just as easy for the client to "fake" or misunderstand checklist questions. This leads to a misdiagnosis.

In contrast, interactive instruments, such as the BTTPLANNER, present a rich, in depth range of behavioral, evaluative and treatment material. Thus, the BTTPLANNER is for the therapist who is both an artist and a technician. As the therapeutic relationship develops during the administration of the BTTPLANNER, quality evaluative, behavioral information begins to appear, which is usually not available except after months of therapy. When used wisely, this material immediately provides the first steps of therapeutic planning.

Because of the nature of the BTTPLANNER, the supportive nature of the therapist, the planned unpredictability of the administrative sequences, and the fun involved in taking the BTTPLANNER, clients are not overwhelmed. The clients may be relieved that the emotional cards are now "out on the table" and be please that they have been honest with themselves and the therapist. Treatment and the therapist are seen more positively, with new hope for direction in their lives.

Because of the large amounts of behavioral data, which emerge during the BTTPLANNER, some general DSM-IV diagnostic information is included in the Appendix. For complete diagnostic criteria information, consult DSM-IV. It is important to note the length of the problems, historical family information, health information, severity of symptoms and degree of functioning. All or most of this behavioral information will come out during the administration of the BTTPLANNER, but it is up to the therapist to put it into a diagnostic/treatment gestalt.

BTTPLANNER Method Instructions

This interactive, evaluative/treatment behavioral instrument will produce psycho/social information about a client that is extremely helpful in treatment planning. It will not only provide behavioral information, helpful in determining a diagnosis and easily compared to the DSM-IV criteria, but it will also provide patterns of internal conflict and social interaction. These behavioral patterns present a gestalt picture, showing how a client describes himself and the probable reasons for his behavior patterns.

In depth psycho/social information will be presented quickly using the BTTPLANNER. It will present the clients' psycho/social, behavioral scripting patterns in a way not otherwise available. It will also help the therapist form an immediate relationship with the client, because both are working together to uncover the diagnosis and plan the treatment. Thus, treatment starts immediately. This saves time and money, as it empowers the client to get something of value from the therapeutic encounter.

The BTTPLANNER is easy to administer, but it must also be administered correctly to achieve maximum clinical benefit. The following fifteen steps in the administration of the BTTPLANNER must be followed in order. While therapists are encouraged to use the behavioral information gleaned from this instrument creatively, it is imperative that they follow the administration of the BTTPLANNER exactly as described. To miss vital steps in the administrative process is to miss the impact of the BTTPLANNER.

The instrument takes about thirty minutes of interaction between therapist and client to gain its impact. Sometimes administration takes a little longer. In addition to following the correct administration process, the therapist must ask the right questions at the appropriate times. It is important to then wait for the client's behavioral response. While there are no "correct" questions and answers, both the questions and the answers become diagnostically and therapeutically very significant. The therapist's use of questions will automatically be guided by how the client responds to the administrative process.

As mentioned previously, the behavioral information gathered by the BTTPLANNER in a very short period of time can form the beginning of a very productive and significant, albeit sometimes brief, therapeutic relationship. Within that therapeutic relationship developed during the instrument's administration, the beginnings of a solid DSM-IV diagnosis can be made, a short or long-term therapeutic relationship can be formed, or the appropriate referral made. When an appropriate referral is made, based upon the client's behavior as registered on the BTTPLANNER, the clients will feel they have been heard, their basic needs have been attended to and they are a part of the referral process itself. This differs greatly from the therapist making a referral, because the Employee Assistance Program or insurance company says that there are only a few sessions available and that a referral is mandatory. With forced referral practice, there is opportunity for client misunderstanding, which leads to a costly and extremely unproductive referral.

The behavioral psycho/social evaluation process of the BTTPLANNER is helpful to both clients and therapists and, hence, to any third party payers. Clients benefit by feeling good. They have directly participated in getting help for themselves when interacting with this instrument. The therapist's practice is strengthened in a variety of ways, including a satisfied client, a more accurate diagnosis, a meaningful referral source for other clients, an intervention done with caring dispatch, a satisfied third party payer, and the satisfaction received from interaction with a client in a positive way.

The administration of the BTTPLANNER is divided into the following sections. While they should be presented in a relaxed, comfortable manner, they must be done in the correct order. Following the procedural steps in the correct order is important because each step builds upon the next. Each conclusion is the result of a progressively more complicated and revealing process.

1. The Setting:

Because it is small and compact, the BTTPLANNER can be administered nearly any place. Possible settings include an office, the client's workplace, home or even jail. It is best to find a place where the client feels safe and comfortable, and that is quiet and confidential.

2. The Explanation:

Make the explanation of the BTTPLANNER as simple and as clear as possible. Explain that the client is to take some cards with descriptive words on them and arrange them in rows under the heading cards. These headings are very specific and also note the number of word cards that should be placed under them. If the client has questions about the meanings of the words, answer simply and clearly. If the client asks where the cards should be placed, state that the arrangement of the cards is up to the client. Explain that there is no correct way to organize the words. The client needs to distribute them in a way that expresses his or her feelings at the moment. (Note: Other than placing the word cards under the heading cards, the only specific requirement is to place the correct number of word cards under the heading cards. The correct number is indicated by the numbers printed on the heading cards.)

3. The Headings:

Lay the five heading cards 10 from left to right in front of the client in the following order: [I Really Am Not (2)] [I Am Not Most of The Time (8)] [I Don't Know If I Am or Not(11)] [I Am Most of The Time(8)] [I Really Am(2)]

Note that each of these heading cards 10 has a number. The number on each of the heading cards 10 will govern the number of word cards 20 in each row. Remember that the heading cards 10 need to be laid out from negative to positive, as shown above. The word cards 20 are to be arranged in rows underneath each heading card 10.

4. Laying down the Cards:

The client is then instructed to lay down the word cards 20 as he or she chooses, in a vertical row under each of the heading cards 10. Encourage the client to lay down all the word cards 20 on his or her first impulse as desired. The client may then change them around so that they match the numbers on the Heading Cards 10. Instruct the client to lay down only the number of cards 20 under the number indicated on the heading cards 10. Thus, two heading cards 10 get 2 word cards 20 each, two headings get 8 word cards 20 each, and the middle column has 11 word cards 20. Once, however, he or she is satisfied with the word card 20 arrangement under the heading cards 10, the cards will remain as placed for the rest of the BTTPLANNER interactive experience.

| [I Really Am Not (2)] | [I Am Not Most of The Time (8)] | [I Don't Know If I Am or Not (11)] | [I Am Most of The Time (8)] | [I Really Am (2)] |
|---|---|---|---|---|
| [~~~] | [~~~] | [~~~] | [~~~] | [~~~] |
| [~~~] | [~~~] | [~~~] | [~~~] | [~~~] |
| | [~~~] | [~~~] | [~~~] | |
| | [~~~] | [~~~] | [~~~] | |
| | [~~~] | [~~~] | [~~~] | |
| | [~~~] | [~~~] | [~~~] | |
| | [~~~] | [~~~] | [~~~] | |
| | [~~~] | [~~~] | [~~~] | |
| | | [~~~] | | |
| | | [~~~] | | |
| | | [~~~] | | |

20

5. The Bell Curve:

Thus, the cards will be distributed as follows: 2, 8, 11, 8, and 2. This makes a Bell Curve. Understanding the proportions of the Bell Curve is important in the administration of the BTTPLANNER. The column with the eleven cards is the median, where the cards seem to be put 5 that don't fit any place else. The columns with two cards each, at the extremes, become the defense mechanisms which might be used infrequently by the client, except when angry or upset. Finally, the columns with eight cards each are the outer limits between which most of the client's usual behavior is described. These two rows of eight cards tend to describe most clearly the client's everyday functioning.

6. Word Card Distribution:

The client lays the word cards under the heading cards, with the therapist giving no response other than supportive empathy. Since there is no right or wrong distribution of the word cards, the client is encouraged to place them wherever desired. After the cards are distributed, the client is asked if he or she wishes to change any of them around. Once the client is satisfied, the Bell Curve distribution is checked for the number placement. After the initial task is finished, the cards remain as distributed for the balance of the test.

7. Word Card Elimination:

The therapist makes note of which word cards are under each Heading Card, as the client briefly describes why the adjective cards were distributed as they are. Getting this information 20 from the client helps the therapist understand how the client sees himself or herself.

The Bell Curve is briefly explained to the client. Since the two cards on each end are used less than two percent of the time, these cards are described as personal defense mechanisms. The therapist turns them over so they cannot be seen, making sure the client understands why the four cards are turned over. Turning the cards over will put the words out of sight and let the client focus on the two columns of eight cards with fewer distractions.

Next, also in relation to the Bell Curve, the therapist explains that the middle row is the average or median. Because of that, most people put all the cards in that column that they feel don't fit anywhere else. When agreement and understanding from the client is obtained, that row of cards is turned over as well, making sure that the client comprehends what is happening before proceeding. Turning this row of cards over permits the client to focus exclusively on the two rows of eight word cards each.

| [I Really Am Not (2)] | [I Am Not Most of The Time (8)] | [I Don't Know If I Am or Not (11)] | [I Am Most of The Time (8)] | [I Really Am (2)] |
|---|---|---|---|---|
| [///////] | [~~~~] | [///////] | [~~~~] | [///////] |
|  | [~~~~] |  | [~~~~] |  |
|  | [~~~~] |  | [~~~~] |  |
|  | [~~~~] |  | [~~~~] |  |
|  | [~~~~] |  | [~~~~] |  |
|  | [~~~~] |  | [~~~~] |  |
|  | [~~~~] |  | [~~~~] |  |
|  | [~~~~] |  | [~~~~] |  |

8. Two Columns of Eight Cards Each:

During the entire BTTPLANNER administration, the client will probably maintain a continuous patter of explanations as to why one card was placed here, and another, there. All that patter is extremely helpful information, which contributes to a more accurate assessment and ultimately diagnosis. But, now in the administration of the BTTPLANNER, the therapist stops and asks the client in more detail why he or she placed the word cards in these two remaining columns. Since all the adjective cards speak to relationships and/or violence, it is easy to tell what the client thinks about himself or herself. Much information is gained about the client's employment and family, as well as psycho/social and historical information. If there are any questions about the client's explanations, the therapist asks what is meant, explaining to the client that understanding what the card distribution means is essential.

By the time the client has removed the complimentary card pairs, there will be two or three remaining cards in each of the two columns, and the client will be talking quite freely and sharing therapeutic information. The remaining two or three cards under the [I Am Most of The Time] heading will demonstrate how the client sees his or her functioning. The therapist asks if the remaining cards in the [I Am Most of The Time] column describe the client. Clients usually expound at some length about how they feel about these remaining two or three cards. More information about the complimentary card selection process is available from the "Kimberly Example". Next turn over the remaining cards in the [I Am Not Most of the Time], explaining that they are negative, and do not need to be used.

| [I Really Am Not (2)] | [I Am Not Most of The Time (8)] | [I Don't Know If I Am or Not (11)] | [I Am Most of The Time (8)] | [I Really Am (2)] |
|---|---|---|---|---|
| [///////] | [~~~~] | [///////] | [~~~~] | [///////] |
|  | [~~~~] |  | [~~~~] |  |
|  | [~~~~] |  | [~~~~] |  |

9. Complimentary Word Cards:

After both the client and therapist understand the distribution of the remaining word cards, the final, and probably most important, part of the test begins. The therapist encourages one more sort of the cards. When the client is ready, he or she is asked to eliminate the complimentary cards in each of the remaining two rows of eight cards each. Explanation is usually necessary. Recognizing that one row is under a negative heading and that the other row is under a positive heading, clarify that the client is to eliminate any two cards that are complimentary. A listing of the thirty-one adjective words, each with all the potential complementary words, is available following the "Example Session with a Client." For example, the following word cards might be complimentary:

| [I Am Not Most of The Time] | [I Am Most of The Time] |
|---|---|
| Distrustful | Trusting |
| Critical | Supportive |
| Passive | Open |
| Afraid | Confident |

10. Defense Mechanisms:

After clients complete the complimentary selection process, they will probably show amazement because they have honestly described themselves. Now that the therapist knows what they are really like (verbally and with the card distribution), the client is asked to pause a minute and think about what happens when they get really frustrated or angry. In response, they will share with the therapist how they behave when frustrated and how sometimes their behavior gets them into trouble.

When the therapist has the client's attention and is familiar with how he or she behaves, the client is asked what happens when he/she gets frustrated. The therapist then turns over the two cards that were placed under [I Really Am] and shares them with the client. Discussion ensues on how these two behaviors work or don't work in protecting their feelings. Next the client is asked what happens when they really get angry. Finally the two cards under the [I Really Am Not] heading are turned over.

| [I Really Am Not (2)] | [I Am Not Most of The Time (8)] | [I Don't Know If I Am or Not (11)] | [I Am Most of The Time (8)] | [I Really Am (2)] |
|---|---|---|---|---|
| [~~~~] | [//////] | [//////] | [~~~~] | [~~~~] |
| [~~~~] |  |  | [~~~~] | [~~~~] |
| Defense |  |  | [~~~~] | Defense |
| Mechanisms |  |  | [~~~~] | Mechanisms |

At this point, the client will be relieved, not only because of his or her emotional catharsis, but also because the therapist seems to completely understand and accept how he or she feels. Furthermore, a relationship is building between them. Therapy has already begun. Any intellectualization that the client has used for years to rationalize behavior, fears, pains, frustrations and anger will no longer be necessary. Now a complete picture of the client's psycho/social functioning is out in the open, in a gentle, loving, supportive atmosphere.

The therapist finally asks the client "How do the adjective words remaining in the "I am Most of the Time {8} column apply to the pattern of your behavior, and is that behavior pattern productive?"

11. What Do Your Want To Do About It?

Then the question is asked, "Now that you know more about yourself, what do you want to do about it?" Because all objections will have been put aside, the client's natural response will be, "I want to fix it." The client may either make some suggestions as to what they want to do or will ask what the therapist recommends. This is a natural point to talk about treatment and the client's involvement in it. Commitment to a mutually agreed upon treatment plan then flows naturally.

12. A Final Step:

A final step in administering the BTTPlanner is to call the attention of the client back to the [I Really Am Not] column. After the second sort, the column usually presents at least one ambiguity, which represents difficulties that are evident in the client's script.

For example, let's say that the cards remaining in that column are Afraid, Listening and Confident. Afraid is not compatible with the other two cards and, thus, sets up an ambiguity, which is probably the source of constant conflict in the client. That conflict tends to short circuit the client's limbic system and not let him/her pay attention to being Listening and Confident.

To resolve this conflict and to begin treatment planning, the therapist may remove the Afraid card and ask the client to again sort through all of the cards that are not used and pick any card to replace it. Usually the client picks a more positive card, a card that is more compatible with Confident and Listening. If this happens, the client is asked what three things need to happen in order for that new card to be integrated with the other two.

For example, if Afraid is replaced by Optimism, ask the client what three things need to happen in order for him/her to be more optimistic. Three things might include:

1. I need to get up earlier.
2. I need to get a job.
3. I need to change my friends While these are very practical things, they are measurable and can be used to begin the process of facilitating change in the client's script. Thus, they are very helpful in not only engaging the client in his/her own therapy but also establishing some measurable, practical beginning steps to that goal.

If the client replaces a negative card with another negative card, this is also very diagnostically significant. In this case, the client is asked for three reasons why that card was chosen. As the client lists those reasons, he/she is asked to prioritize the three reasons. When this is done, the therapist inquires about three steps that might be necessary for the client to take in order to make the script more compatible.

Thus, again the client is participating, and the therapist is helping to increase the healthy productivity of his/her functioning.

13. DSM-IV:

The professional therapist, using this tool, needs to be familiar with DSM-IV and how a diagnosis relates to a client's behavior pattern. Some diagnostic information is included following the "Example Session with a Client."

14. Level Of Functioning:

When using the BTTPLANNER, the therapist should be able to establish the DSM-IV level of functioning, the defenses used, and the amount of enthusiasm or lack of it. If there are any further questions of the client and the level of functioning, now is the time to ask.

15. Health:

As the therapist went through the BTTPLANNER material, the client has probably told about health issues and any medication being taken. This data should be double checked, making sure the therapist knows the name of the client's physician and about health problems and medications. Of course, this medical information can be very helpful in planning treatment or making a referral. Gaining this information is an important adjunct to the psycho/social material acquired during the administration of the BTTPLANNER.

16. Conclusions:

There are many conclusions that can be drawn when gathering data from the client using the BTTPLANNER. The exact information depends upon the therapist, the client and the interactive experience that they have had together. The therapist will be well on his/her way with a mutually acceptable diagnosis and a treatment plan. The therapist will know about the client's defenses, what further information to gather about addictions, and some of the family dynamics. The therapist will also know if the client feels that there is a supportive family system around, which, of course, is very important in treatment, particularly if the client is depressed.

The therapist will also be able to draw some conclusions about his/her ability to relate to this particular client. It is important that the therapist understands his/her feelings about the client and the client's behavior before deciding whether or not to form a more intense therapeutic relationship and begin treatment.

EXAMPLE SESSION WITH A CLIENT

The following example is the sorting that Kimberly made with her cards, using the BTTPLANNER, prior to the revision of this test. You will notice some differences between the sort made by Kimberly and the test described previously, but the concepts are similar.

I Really Am Not
   Trusting, Inattentive.
I Am Not Most of the Time
   Critical, Aware, Dishonest, Confident, Threatened, Passive.
I Am All the Time (replaced by I Don't Know If I Am or Not)
   Open, Afraid, Distrustful, Aware, Manipulate, Jealous, Hyper, Supportive, Defensive.
I Am Most of the Time
   Distracted, Listening, Laughing, Friendly, Impulsive, Insecure.
I Really Am All the Time
   Compassionate, Kind.

If the therapist looks just at her distribution of the cards, he/she would think that Kimberly sees herself as compassionate and kind. That is what she thought as she laid out the cards, grinned, and emphatically stated, "Yes." She had finished the card distribution, and it was correct.

The Bell Curve was explained to her, which she understood easily, because she got an "A" in her college statistics class. She, however, now began to wonder what else was going to happen.

Kimberly understood the average or median and why the middle row of cards was removed. She knew that row was where she put most of the cards she didn't feel belonged anywhere else. She also understood taking off the two end rows. From a statistical point of view, she used them only a small percentage of the time.

That left the two rows, I Am Not Most of the Time and I Am Most of the Time. Now she began to smile, knowing that there was something in this experience that she hadn't figured out yet.

After she had picked out the complimentary cards in these two columns, the only cards left were Listening, Laughing, and Impulsive, all under I Am Most of the Time.

Now she knew what was happening and became self-conscious, teary eyed, giggly and somewhat vulnerable. Thus, her scenario goes, "When I listen and hear something that I do not like, I am afraid of, or I feel insecure about, I either laugh to cover up my insecurity or act out impulsively." Thus, on one level, she could be diagnosed as an Attention Deficit Disorder Adult because of her history and her constant impulsivity.

Then the I Really Am All the Time cards, Compassionate and Kind were turned over. She immediately laughed and responded that when she gets caught acting out in some impulsive manner, she becomes compassionate and kind to cover up her behavior, to manipulate others, and to get out of any jam into which she may have gotten herself.

While this information made Kimberly somewhat agitated, she understood and readily admitted that the cards were correct. Then she was told that there was one more way to link to the drama of her life, and the two cards under I Really Am Not All the Time, Trusting and Inattentive, were turned over. Thus, when she really gets into a bind, and Compassionate and Kind do not adequately cover up her impulsivity and disorganization, she verbalizes to herself and to others that she is not going to pay attention because she does not trust anyone.

This might be called the real Kimberly. She is a woman who grew up in a dysfunctional environment, never trusting and learning to manipulate. She never has had satisfactory 5 relationships with anyone. She describes herself as pathetic, even though she is an intelligent and attractive college graduate, who owns her own business and displays a variety of superficial social skills.

Diagnosis

On the surface, Kim has many ADD-Adult symptoms, and they have existed for an extended period. She had trouble in school, could not sit still and pay attention, in addition to most of the other symptoms listed in DSM-IV. Therefore, she has been diagnosed as ADD-Adult and given Ritalin. The Ritalin, however, didn't work because it didn't address the real problem and because it fit with her other addictions. She has been addicted to alcohol, drugs, impulsivity, Harley Davidsons, sex and disorganization. Thus, the Ritalin, while it helped for a short time, only made matters worse.

One could also diagnose Kim with depression. She certainly has been depressed, acted impulsively when depressed, and slept most of the time. Sometimes she did not groom herself adequately and hated being around people, although she has more than adequate social skills. She was prescribed an antidepressant, which helped for a while, but because of her addictions, the medication only made the problem worse.

As the therapist looked closely, however, in trying to diagnose and treat Kimberly, it became apparent that she has little trust in anyone and only a few satisfactory relationships. She also has been addicted to distrusting behavior. Because of her addiction patterns, Ritalin and/or Zoloft exacerbate her lack of trust.

The bright spot, which she brought up in this diagnostic process and beginning of her treatment, is her seedlings of trust she has recently begun with her husband and her father. This was positive and insightful on Kimberly's part and a beginning personal course of action. In other words, Kimberly understood that she really needed to get better. She willingly started on her wellness journey, leaving behind the addiction journey, which had lasted for thirty plus years.

There are numerous diagnostic and treatment implications in Kimberly's journey, some of which are mentioned.

1. Kimberly has been difficult to diagnose.
2. Kimberly has self-medicated herself with a variety of things like alcohol, drugs and getting high from her impulsivity. Prescribed medications tend only to exacerbate this process.
3. Kimberly has viewed herself as pathetic, even though she is just the opposite. It is almost like her "patheticness" is also an addiction, a habit or a lifestyle. Actually, it probably is an unsatisfactory defense mechanism.
4. Kimberly took a giant therapeutic stride when she volunteered to take the BTTPLANNER, to have the experience recorded, and then to be used as a demonstration tape to help therapists learn to administer the instrument. It shows a beginning trust in herself, as well as in her therapist.
5. Kimberly now has a different attitude about herself. She knows that she has a therapeutic road to travel. But she is willing to take some responsibility for it herself, instead of being dependent on prescriptions or self-medication. Both have proven over a long period of time to exacerbate her problems.

6. Kimberly's diagnosis and her involvement in her treatment plan make the treatment cost-effective. She can be seen in therapy for the purpose of some insight and support so she can get better. This is, in contrast, to only medicine management, which would only exacerbate her behaviors. Ultimately, Kimberly would end up in the hospital and have lots of medical bills. At that point she might legitimately see herself as pathetic.
7. Kimberly now has hope, which is a goal in therapy.

Word Definitions a.fraid adj. Filled with fear. Having feelings of aversion or unwillingness in regard to something. Filled with regret or concern. Used especially to soften an unpleasant statement.

a.ware adj. Having knowledge or cognizance: aware of their limitations. Archaic. Vigilant; watchful.

a.voiding adj. Stay clear of; shunning. Withdrawing to keep something from happening.

com.pas.sion.ate adj. 1. Feeling or showing compassion; sympathetic. Tender, gentle, kind.

con.fi.dent adj. Marked by assurance. Self-assured.

crit.i.cal adj. Inclined to judge severely and find fault.

de.fen.sive adj. Protective. Intended to withstand or deter aggression or attack.

dis.hon.est adj. Disposed to lie, cheat, defraud, or deceive. Resulting from or marked by a lack of honesty.

dis.tract.ed adj. Having the attention diverted. Suffering conflicting emotions; distraught.

dis.trust.ful adj. Feeling or showing doubt.

for.giv.ing adj. Able to excuse a wrong or dismiss charges.

friend.ly adj. Of, relating to, or befitting a friend. Favorably disposed; not antagonistic. Warm; comforting.

hate.ful adj. Acting in an offensive, loathsome, detestable manner.

help.ing adj. Giving assistance, aid, support or advice. Working with. Co-operating with.

hy.per adj. Slang. Having a very excitable or nervous temperament; high-strung. Emotionally stimulated or overexcited. [Short for hyperactive.]

im.pul.sive adj. Inclined to act on impulse rather than thought. Motivated by or resulting from impulse. Having force or power to impel or incite; forceful.

in.at.ten.tive adj. Lacking the ability to pay attention, notice, or regard.

in.se.cure adj. Not sure or certain; doubtful. Inadequately guarded or protected; unsafe. Not firm or fixed; unsteady. Lacking emotional stability; not well-adjusted. Lacking self-confidence; plagued by anxiety.

jeal.ous adj. Fearful or wary of being supplanted; apprehensive of losing affection or position. Resentful or bitter in rivalry; envious. Inclined to suspect rivalry. Having to do with or arising from feelings of envy, apprehension, or bitterness. Vigilant in guarding something.

kind adj. Of a friendly, generous, or warm-hearted nature. Showing sympathy or understanding; charitable: a kind word. Humane; considerate. Forbearing; tolerant.

laughing adj. Expressing certain emotions, especially mirth, delight, or derision, by a series of spontaneous, usually unarticulated sounds often accompanied by corresponding facial and bodily movements. Showing or feeling amusement or good humor.

lis.tening adj. Making an effort to hear something. Paying attention; heed.

ma.nip.u.la.tive adj. Influencing or managing shrewdly or deviously. Tampering with or falsifying for personal gain.

o.pen adj. Uncorrupted, undecided, undetermined.

op.ti.mis.tic adj. Cheerful, hopeful, upbeat.

pas.sive adj. Receiving or subjected to an action without responding or initiating an action in return. Accepting or submitting without objection or resistance; compliant. Not participating, acting, or operating; inert.

pes.si.mis.tic adj. Despairing, morbid, gloomy, discouraging.

re.venge.ful adj. Spiteful, vindictive, malicious.

sup.por.tive adj. Furnishing support or assistance. Encouraging, sympathetic, offering, moral support.

threat.ened adj. In jeopardy. At risk of becoming endangered.

trusting adj. Firm reliance on the integrity, ability, or character of another. Accepting, believing, confident, convinced.

| Words that Build Relationships | |
|---|---|
| A. | Listening |
| B. | Confident |
| C. | Trusting |
| D. | Open |
| E. | Laughing |
| F. | Kind |
| G. | Supportive |
| H. | Friendly |
| I. | Aware |
| J. | Compassionate |
| K. | Forgiving |
| L. | Helping |
| M. | Optimistic |
| Words that Break Relationships | |
| N. | Passive |
| O. | Distrustful |
| P. | Avoiding |
| Q. | Insecure |
| R. | Dishonest |
| S. | Manipulative |
| T. | Defensive |
| U. | Afraid |
| V. | Threatened |
| W. | Jealous |
| X. | Critical |
| Y. | Hateful |
| Z. | Revengeful |
| AA. | Pessimistic |
| Impulsive, Non-productive Words | |
| BB. | Inattentive |
| CC. | Distracted |
| DD. | Hyper |
| EE. | Impulsive |

| Complimentary Words for the BTTPlanner ™ | |
|---|---|
| I Am Most Of The Time | Complimentary Words |
| Afraid | Aware |
| | Compassionate |
| | Confident |
| | Forgiving |
| | Friendly |
| | Helping |
| | Kind |
| | Listening |
| | Open |
| | Optimistic |
| | Supportive |
| | Trusting |

-continued

Complimentary Words for the BTTPlanner ™

| I Am Most Of The Time | Complimentary Words |
|---|---|
| Avoiding | Aware |
|  | Compassionate |
|  | Confident |
|  | Forgiving |
|  | Friendly |
|  | Helping |
|  | Kind |
|  | Laughing |
|  | Listening |
|  | Open |
|  | Optimistic |
|  | Supportive |
|  | Trusting |
| Aware | Afraid |
|  | Avoiding |
|  | Critical |
|  | Defensive |
|  | Dishonest |
|  | Distracted |
|  | Distrustful |
|  | Hateful |
|  | Hyper |
|  | Impulsive |
|  | Inattentive |
|  | Insecure |
|  | Jealous |
|  | Manipulative |
|  | Passive |
|  | Pessimistic |
|  | Revengeful |
|  | Threatened |
| Compassionate | Afraid |
|  | Avoiding |
|  | Critical |
|  | Defensive |
|  | Dishonest |
|  | Distracted |
|  | Distrustful |
|  | Hateful |
|  | Impulsive |
|  | Inattentive |
|  | Insecure |
|  | Jealous |
|  | Manipulative |
|  | Passive |
|  | Pessimistic |
|  | Revengeful |
|  | Threatened |
| Confident | Afraid |
|  | Avoiding |
|  | Critical |
|  | Defensive |
|  | Dishonest |
|  | Distracted |
|  | Distrustful |
|  | Hateful |
|  | Hyper |
|  | Impulsive |
|  | Inattentive |
|  | Insecure |
|  | Jealous |
|  | Laughing |
|  | Manipulative |
|  | Passive |
|  | Pessimistic |
|  | Revengeful |
|  | Threatened |
| Critical | Aware |
|  | Compassionate |
|  | Confident |
|  | Forgiving |
|  | Friendly |
|  | Helping |
|  | Kind |

-continued

Complimentary Words for the BTTPlanner ™

| I Am Most Of The Time | Complimentary Words |
|---|---|
|  | Listening |
|  | Open |
|  | Optimistic |
|  | Supportive |
|  | Trusting |
| Defensive | Aware |
|  | Compassionate |
|  | Confident |
|  | Forgiving |
|  | Friendly |
|  | Helping |
|  | Kind |
|  | Listening |
|  | Open |
|  | Optimistic |
|  | Supportive |
|  | Trusting |
| Dishonest | Aware |
|  | Compassionate |
|  | Confident |
|  | Forgiving |
|  | Friendly |
|  | Helping |
|  | Kind |
|  | Open |
|  | Supportive |
|  | Trusting |
| Distracted | Aware |
|  | Compassionate |
|  | Confident |
|  | Forgiving |
|  | Friendly |
|  | Helping |
|  | Kind |
|  | Listening |
|  | Open |
|  | Optimistic |
|  | Supportive |
|  | Trusting |
| Distrustful | Aware |
|  | Compassionate |
|  | Confident |
|  | Forgiving |
|  | Friendly |
|  | Helping |
|  | Kind |
|  | Listening |
|  | Open |
|  | Optimistic |
|  | Supportive |
|  | Trusting |
| Forgiving | Afraid |
|  | Avoiding |
|  | Critical |
|  | Defensive |
|  | Dishonest |
|  | Distracted |
|  | Distrustful |
|  | Hateful |
|  | Hyper |
|  | Impulsive |
|  | Inattentive |
|  | Insecure |
|  | Jealous |
|  | Laughing |
|  | Manipulative |
|  | Passive |
|  | Pessimistic |
|  | Revengeful |
|  | Threatened |
| Friendly | Afraid |
|  | Avoiding |
|  | Critical |
|  | Defensive |

Complimentary Words for the BTTPlanner ™

| I Am Most Of The Time | Complimentary Words |
|---|---|
| | Dishonest |
| | Distracted |
| | Distrustful |
| | Hateful |
| | Hyper |
| | Impulsive |
| | Inattentive |
| | Insecure |
| | Jealous |
| | Manipulative |
| | Passive |
| | Pessimistic |
| | Revengeful |
| | Threatened |
| Hateful | Aware |
| | Compassionate |
| | Confident |
| | Forgiving |
| | Friendly |
| | Helping |
| | Kind |
| | Listening |
| | Open |
| | Optimistic |
| | Supportive |
| | Trusting |
| Helping | Afraid |
| | Avoiding |
| | Critical |
| | Defensive |
| | Dishonest |
| | Distracted |
| | Distrustful |
| | Hateful |
| | Hyper |
| | Impulsive |
| | Inattentive |
| | Insecure |
| | Jealous |
| | Laughing |
| | Manipulative |
| | Passive |
| | Pessimistic |
| | Revengeful |
| | Threatened |
| Hyper | Aware |
| | Compassionate |
| | Confident |
| | Forgiving |
| | Friendly |
| | Helping |
| | Listening |
| | Open |
| | Passive |
| | Supportive |
| | Trusting |
| Impulsive | Aware |
| | Compassionate |
| | Confident |
| | Forgiving |
| | Friendly |
| | Helping |
| | Kind |
| | Listening |
| | Open |
| | Supportive |
| | Trusting |
| Inattentive | Aware |
| | Compassionate |
| | Confident |
| | Forgiving |
| | Friendly |
| | Helping |
| | Kind |

Complimentary Words for the BTTPlanner ™

| I Am Most Of The Time | Complimentary Words |
|---|---|
| | Listening |
| | Open |
| | Optimistic |
| | Supportive |
| | Trusting |
| Insecure | Aware |
| | Compassionate |
| | Confident |
| | Forgiving |
| | Friendly |
| | Helping |
| | Kind |
| | Listening |
| | Open |
| | Optimistic |
| | Supportive |
| | Trusting |
| Jealous | Aware |
| | Compassionate |
| | Confident |
| | Forgiving |
| | Friendly |
| | Helping |
| | Kind |
| | Listening |
| | Open |
| | Optimistic |
| | Supportive |
| | Trusting |
| Kind | Avoiding |
| | Critical |
| | Defensive |
| | Dishonest |
| | Distracted |
| | Distrustful |
| | Hateful |
| | Hyper |
| | Impulsive |
| | Inattentive |
| | Insecure |
| | Jealous |
| | Laughing |
| | Manipulative |
| | Passive |
| | Pessimistic |
| | Revengeful |
| Laughing | Aware |
| | Compassionate |
| | Confident |
| | Forgiving |
| | Friendly |
| | Helping |
| | Listening |
| | Open |
| | Optimistic |
| | Passive |
| | Supportive |
| | Trusting |
| Listening | Afraid |
| | Avoiding |
| | Critical |
| | Defensive |
| | Dishonest |
| | Distracted |
| | Distrustful |
| | Hateful |
| | Hyper |
| | Impulsive |
| | Inattentive |
| | Insecure |
| | Jealous |
| | Laughing |
| | Manipulative |
| | Passive |

Complimentary Words for the BTTPlanner ™

| I Am Most Of The Time | Complimentary Words |
|---|---|
| Manipulative | Pessimistic |
| | Revengeful |
| | Aware |
| | Compassionate |
| | Confident |
| | Forgiving |
| | Friendly |
| | Helping |
| | Kind |
| | Listening |
| | Open |
| | Optimistic |
| | Supportive |
| | Trusting |
| Open | Afraid |
| | Avoiding |
| | Critical |
| | Defensive |
| | Dishonest |
| | Distracted |
| | Distrustful |
| | Hateful |
| | Hyper |
| | Impulsive |
| | Inattentive |
| | Insecure |
| | Jealous |
| | Laughing |
| | Manipulative |
| | Passive |
| | Pessimistic |
| | Revengeful |
| | Threatened |
| Optimistic | Avoiding |
| | Critical |
| | Defensive |
| | Distrustful |
| | Hateful |
| | Insecure |
| | Jealous |
| | Manipulative |
| | Pessimistic |
| | Revengeful |
| | Threatened |
| Passive | Aware |
| | Compassionate |
| | Confident |
| | Forgiving |
| | Friendly |
| | Helping |
| | Kind |
| | Listening |
| | Open |
| | Optimistic |
| | Supportive |
| | Trusting |
| Pessimistic | Aware |
| | Compassionate |
| | Confident |
| | Forgiving |
| | Friendly |
| | Helping |
| | Kind |
| | Open |
| | Optimistic |
| | Supportive |
| | Trusting |
| Revengeful | Aware |
| | Compassionate |
| | Confident |
| | Forgiving |
| | Friendly |
| | Helping |
| | Kind |
| | Listening |
| | Open |
| | Optimistic |
| | Supportive |
| | Trusting |
| Supportive | Afraid |
| | Avoiding |
| | Critical |
| | Defensive |
| | Dishonest |
| | Distracted |
| | Distrustful |
| | Hateful |
| | Impulsive |
| | Inattentive |
| | Insecure |
| | Jealous |
| | Manipulative |
| | Passive |
| | Pessimistic |
| | Revengeful |
| | Threatened |
| Threatened | Aware |
| | Compassionate |
| | Confident |
| | Forgiving |
| | Friendly |
| | Helping |
| | Kind |
| | Listening |
| | Open |
| | Optimistic |
| | Supportive |
| | Trusting |
| Trusting | Avoiding |
| | Critical |
| | Defensive |
| | Dishonest |
| | Distracted |
| | Distrustful |
| | Hateful |
| | Inattentive |
| | Insecure |
| | Jealous |
| | Manipulative |
| | Passive |
| | Pessimistic |
| | Revengeful |
| | Threatened |

DSM-IV Attention Deficit Disorder

The DSM-IV general criteria for Attention Deficit Disorder are:

Six or more of the following symptoms of inattention have persisted for at least six months to a degree that is maladaptive.

Inattention
1. Often fails to give close attention to details.
2. Often has difficulty in sustaining attention.
3. Often does not seem to listen.
4. Often dose not follow through on instructions.
5. Often has difficulty organizing tasks and activities.
6. Often avoids tasks that require sustained mental effort.
7. Often loses things.
8. Often distracted.
9. Often forgetful.

Hyperactivity

Six of the symptoms have persisted for at least six months to a maladaptive degree.
1. Often fidgets.
2. Often leaves seat, when should remain seated.
3. Often runs about or climbs excessively.
4. Often has difficulty in engaging in leisure time activities quietly.
5. Often on the go as if "driven by a motor."
6. Often talks excessively Impulsivity
1. Often blurts out answers before questions have been completed.
2. Often has difficulty awaiting his turn.
4. Often interrupts or intrudes on others.

DSM-IV Depression

The DSM-IV criteria for Depression are:
Five or more of the following have been present during the same two-week period and represent a change in previous functioning.
1. Depressed mood most of the day.
2. Markedly diminished interest or pleasure in almost all activities most of the day, nearly every day.
3. Significant weight loss.
4. Insomnia or hypersomnia nearly every day.
5. Psychomotor agitation or retardation nearly every day.
6. Fatigue or loss of energy nearly every day.
7. Feelings of worthlessness or excessive or inappropriate guilt.
8. Diminished ability to think or concentrate.
9. Recurrent thoughts of death While the present invention has been described with reference to several particular example embodiments, those skilled in the art will recognize that many changes may be made thereto without departing from the spirit and scope of the present invention.

We claim:

1. A set of cards for interactive psycho/social evaluation of a client individual by a therapist comprising;
   a first subset of five heading cards, each heading card having one of the phrases;
   (a) "I Really Am Not {2}";
   (b) "I Am Not Most of the Time {8}";
   (c) "I Do Not Know If I Am or Not {11}";
   (d) "I Am Most of the Time {8}";
   (e) "I Really Am {2}"; and
   a second subset of thirty-one adjective cards, each adjective card having a different one of the words;
   (A) Listening; (B) Confident; (C) Trusting; (D) Open; (E) Laughing; (F) Kind; (G) Supportive; (H) Friendly; (I) Aware; (J) Compassionate; (K) Forgiving; (L) Helping; (M) Optimistic; (N) Passive; (O) Distrustful; (P) Avoiding; (Q) Insecure; (R) Dishonest; (S) Manipulative; (T) Defensive; (U) Afraid; (V) Threatened; (W) Jealous; (X) Critical; (Y) Hateful; (Z) Revengeful; (AA) Pessimistic; (BB) Inattentive; (CC) Distracted; (DD) Hyper; (EE) Impulsive.

2. A method of interactive psycho/social evaluation of a client individual by a therapist comprising;
   (a) providing a first set of five column headings, each heading having one of the phrases;
   (i) "I Really Am Not {2}";
   (ii) "I Am Not Most of the Time {8}";
   (iii) "I Do Not Know If I Am or Not {11}";
   (iv) "I Am Most of the Time {8}";
   (v) "I Really Am {2}";
   (b) providing a second set of thirty-one adjective words;
   (A) Listening; (B) Confident; (C) Trusting; (D) Open; (E) Laughing; (F) Kind; (G) Supportive; (H) Friendly; (I) Aware; (J) Compassionate; (K) Forgiving; (L) Helping; (M) Optimistic; (N) Passive; (0) Distrustful; (P) Avoiding; (Q) Insecure; (R) Dishonest; (S) Manipulative; (T) Defensive; (U) Afraid; (V) Threatened; (W) Jealous; (X) Critical; (Y) Hateful; (Z) Revengeful; (AA) Pessimistic; (BB) Inattentive; (CC) Distracted; (DD) Hyper; (EE) Impulsive;
   (c) forming five separate columns, each column having one of the column heading phrases therein from the first set;
   (d) distributing, by the client individual, each of the thirty-one adjective words from the second set into one of the five separate columns with a heading therein, the number of adjective words distributed in each column corresponding to the number in parenthesis of each column heading, the individual adjective words each distributed into one of the five columns by the client individual matching the adjective word with the phrase of the heading therein;
   (e) obscuring the adjective words distributed in columns having the headings "I Really Am Not {2}", "I Do Not Know If I Am or Not {11}", and "I Really Am {2}";
   (f) removing, be the client individual, complementary word pairs from columns having the headings "I Am Not Most of the Time {8}", and "I Am Most of the Time {8}", one word of each complementary pair found in each column;
   (g) obscuring the adjective words remaining in the column having the heading "I Am Not 30 Most of the Time {8}";
   (h) asking the client individual "Do the adjective words remaining in the column having the heading "I Am Most of The Time {8}" describe you?";
   (i) asking the client individual "How do you behave when frustrated?", and revealing the adjective words in the column having the heading "I Really Am {2}";
   (j) asking the client individual "How do you behave when angry?", and revealing the adjective words in the column having the heading "I Really Am Not {2}"; and
   (k) asking the client individual "How do the adjective words remaining in the "I Am Most of the Time {8}" column apply to the pattern of your behavior, and is that behavior pattern productive?".

3. A method of interactive psycho/social evaluation of a client individual by a therapist according to claim 2 wherein, the five separate column headings are arranged in the order: "I Really Am Not {2}"; "I Am Not Most of the Time {8}"; "I Do Not Know If I Am or Not {11}"; "I Am Most of the Time {8}"; and "I Really Am {2}".

4. A method of interactive psycho/social evaluation of a client individual by a therapist according to claim 2 wherein, the five separate column headings and the thirty-one adjective words are provided in a printed medium.

5. A method of interactive psycho/social evaluation of a client individual by a therapist according to claim 2 wherein, the five separate column headings and the thirty-one adjective words are provided on a video screen.

6. A method of interactive psycho/social evaluation of a client individual by a therapist according to claim 2 wherein, a complementary word for the word "Afraid" is selected from the group consisting of Aware, Compassionate, Confident, Forgiving, Friendly, Helping, Kind, Listening, Open, Optimistic, Supportive, and Trusting;

and wherein, a complementary word for the word "Avoiding" is selected from the group consisting of Aware, Compassionate, Confident, Forgiving, Friendly, Helping, Kind, Laughing, Listening, Open, Optimistic, Supportive, and Trusting;

and wherein, a complementary word for the word "Aware" is selected from the group Consisting of Afraid, Avoiding, Critical, Defensive, Dishonest, Distracted, Distrustful, Hateful, Hyper, Impulsive, Inattentive, Insecure, Jealous, Manipulative, Passive, Pessimistic, Revengeful, and Threatened;

and wherein, a complementary word for the word "Compassionate" is selected from the group consisting of Afraid, Avoiding, Critical, Defensive, Dishonest, Distracted, Distrustful, Hateful, Impulsive, Inattentive, Insecure, Jealous, Manipulative, Passive, Pessimistic, Revengeful, and Threatened;

and wherein, a complementary word for the word "Compassionate" is selected from the group consisting of Afraid, Avoiding, Critical, Defensive, Dishonest, Distracted, Distrustful, Hateful, Impulsive, Inattentive, Insecure, Jealous, Manipulative, Passive, Pessimistic, Revengeful, and Threatened;

and wherein, a complementary word for the word "Confident" is selected from the group consisting of Afraid, Avoiding, Critical, Defensive, Dishonest, Distracted, Distrustful, Hateful, Hyper, Impulsive, Inattentive, Insecure, Jealous, Laughing, Manipulative, Passive, Pessimistic, Revengeful, and Threatened; and wherein, a complementary word for the word "Critical" is selected from the group consisting of Aware, Compassionate, Confident, Forgiving, Friendly, Helping, Kind, Listening, Open, Optimistic, Supportive, and Trusting;

and wherein, a complementary word for the word "Defensive" is selected from the group consisting of Aware, Compassionate, Confident, Forgiving, Friendly, Helping, Kind, Listening, Open, Optimistic, Supportive, and Trusting;

and wherein, a complementary word for the word "Dishonest" is selected from the group consisting of Aware, Compassionate, Confident, Forgiving, Friendly, Helping, Kind, Open, Supportive, and Trusting;

and wherein, a complementary word for the word "Distracted" is selected from the group consisting of Aware, Compassionate, Confident, Forgiving, Friendly, Helping, Kind, Listening, Open, Optimistic, Supportive, and Trusting;

and wherein, a complementary word for the word "Distrustful" is selected from the group consisting of Aware, Compassionate, Confident, Forgiving, Friendly, Helping, Kind, Listening, Open, Optimistic, Supportive, and Trusting;

and wherein, a complementary word for the word "Forgiving" is selected from the group consisting of Afraid, Avoiding, Critical, Defensive, Dishonest, Distracted, Distrustful, Hateful, Hyper, Impulsive, Inattentive, Insecure, Jealous, Laughing, Manipulative, Passive, Pessimistic, Revengeful, and Threatened;

and wherein, a complementary word for the word "Friendly" is selected from the group consisting of Afraid, Avoiding, Critical, Defensive, Dishonest, Distracted, Distrustful, Hateful, Hyper, Impulsive, Inattentive, Insecure, Jealous, Manipulative, Passive, Pessimistic, Revengeful, and Threatened;

and wherein, a complementary word for the word "Hateful" is selected from the group consisting of Aware, Compassionate, Confident, Forgiving, Friendly, Helping, Kind, Listening, Open, Optimistic, Supportive, and Trusting;

and wherein, a complementary word for the word "Helping" is selected from the group consisting of Afraid, Avoiding, Critical, Defensive, Dishonest, Distracted, Distrustful, Hateful, Hyper, Impulsive, Inattentive, Insecure, Jealous, Laughing, Manipulative, Passive, Pessimistic, Revengeful, and Threatened;

and wherein, a complementary word for the word "Hyper" is selected from the group consisting of Aware, Compassionate, Confident, Forgiving, Friendly, Helping, Listening, Open, Optimistic, Passive, Supportive, and Trusting.

7. A method of interactive psycho/social evaluation of a client individual by a therapist according to claim 2 wherein, a complementary word for the word "Impulsive" is selected from the group consisting of Aware, Compassionate, Confident, Forgiving, Friendly, Helping, Kind, Listening, Open, Supportive, and Trusting;

and wherein, a complementary word for the word "Insecure" is selected from the group consisting of Aware, Compassionate, Confident, Forgiving, Friendly, Helping, Kind, Listening, Open, Supportive, and Trusting;

and wherein, a complementary word for the word "Jealous" is selected from the group consisting of Aware, Compassionate, Confident, Forgiving, Friendly, Helping, Kind, Listening, Open, Optimistic, Supportive, and Trusting;

and wherein, a complementary word for the word "Kind" is selected from the group consisting of Avoiding, Critical, Defensive, Dishonest, Distracted, Distrustful, Hateful, Hyper, Impulsive, Inattentive, Insecure, Jealous, Laughing, Manipulative, Passive, Pessimistic, and Revengeful;

and wherein, a complementary word for the word "Laughing" is selected from the group consisting of Aware, Compassionate, Confident, Forgiving, Friendly, Helping, Kind, Listening, Open, Optimistic, Passive, Supportive, and Trusting;

and wherein, a complementary word for the word "Listening" is selected from the group consisting of Afraid, Avoiding, Critical, Defensive, Dishonest, Distracted, Distrustful, Hateful, Hyper, Impulsive, Inattentive, Insecure, Jealous, Laughing, Manipulative, Passive, Pessimistic, Revengeful, and Threatened;

and wherein, a complementary word for the word "Manipulative" is selected from the group consisting of Aware, Compassionate, Confident, Forgiving, Friendly, Helping, Kind, Listening, Open, Optimistic, Supportive, and Trusting; and wherein, a complementary word for the word "Open" is selected from the group consisting of Afraid, Avoiding, Critical, Defensive, Dishonest, Distracted, Distrustful, Hateful, Hyper, Impulsive, Inattentive, Insecure, Jealous, Laughing, Manipulative, Passive, Pessimistic, Revengeful, and Threatened;

and wherein, a complementary word for the word "Optimistic" is selected from the group consisting of Avoiding, Critical, Defensive, Distrustful, Hateful, Insecure, Jealous, Manipulative, Pessimistic, Revengeful, and Threatened;

and wherein, a complementary word for the word "Passive" is selected from the group consisting of Aware, Compassionate, Confident, Forgiving, Friendly, Helping, Kind, Listening, Open, Optimistic, Supportive, and Trusting;

and wherein, a complementary word for the word "Pessimistic" is selected from the group consisting of Aware, Compassionate, Confident, Forgiving, Friendly, Helping, Kind, Open, Optimistic, Supportive, and Trusting;

and wherein, a complementary word for the word "Revengeful" is selected from the group consisting of Aware, Compassionate, Confident, Forgiving, Friendly, Helping, Kind, Listening, Open, Optimistic, Supportive, and Trusting;

and wherein, a complementary word for the word "Supportive" is selected from the group consisting of Afraid, Avoiding, Critical, Defensive, Dishonest, Distracted, Distrustful, Hateful, Impulsive, Inattentive, Insecure, Jealous, Manipulative, Passive, Pessimistic, Revengeful, and Threatened;

and wherein, a complementary word for the word "Threatened" is selected from the group consisting of Aware, Compassionate, Confident, Forgiving, Friendly, Helping, Kind, Listening, Open, Optimistic, Supportive, and Trusting;

and wherein, a complementary word for the word "Trusting" is selected from the group consisting of Avoiding, Critical, Defensive, Dishonest, Distrustful, Hateful, Inattentive, Insecure, Jealous, Manipulative, Passive, Pessimistic, Revengeful, and Threatened.

8. A method of interactive psycho/social evaluation of a client individual by a therapist comprising;
 (a) providing a set of cards comprising;
  (i) a first subset of five heading cards, each heading card having one of the phrases;
   (a) "I Really Am Not {2}";
   (b) "I Am Not Most of the Time {8}";
   (c) "I Do Not Know If I Am or Not { }";
   (d) "I Am Most of the Time {8}",
   (e) "I Really Am {2}"; and
  (ii) a second subset of thirty-one adjective word cards, each adjective card having one of the words;
   (A) Listening; (B) Confident; (C) Trusting; (D) Open; (E) Laughing; (F) Kind; (G) Supportive; (H) Friendly; (I) Aware; (J) Compassionate; (K) Forgiving; (L) Helping; (M) Optimistic; (N) Passive; (O) Distrustful; (P) Avoiding; (Q) Insecure; (R) Dishonest; (S) Manipulative; (T) Defensive; (J) Afraid; (V) Threatened; (W) Jealous; (X) Critical; (Y) Hateful; (Z) Revengeful; (AA) Pessimistic; (BB) Inattentive; (CC) Distracted; (DD) Hyper; (EE) Impulsive;
 (b) forming five separate columns, each column having one of the heading cards therein from the first subset;
 (c) distributing, by the client individual, each of the thirty-one adjective cards from the second subset into one of the five separate columns with a heading card therein, the number of adjective cards distributed in each column corresponding to the number in parenthesis of each column heading card, the individual adjective cards each distributed into one of the five columns by the client individual matching the adjective word with the phrase of the heading card therein;
 (d) obscuring the adjective cards distributed in columns having the heading cards "I Really Am Not {2}", "I Do Not Know If I Am or Not {11}" and I Really Am {2}";
 (e) removing, be the client individual, complementary word card pairs from columns having the heading cards "I Am Not Most of the Time {8}", and "I Am Most of the Time {8}", one card of the complementary pair found in each column;
 (f) obscuring the adjective cards remaining in the column having the heading card "I Am Not Most of the Time {8}",
 (g) asking the client individual "Do the adjective word cards remaining in the column having the heading card "I Am Most of The Time {8}" describe you?";
 (h) asking the client individual "How do you behave when frustrated?", and revealing the adjective word cards in the column having the heading card "I Really Am {2}";
 (i) asking the client individual "How do you behave when angry?", and revealing the adjective word cards in the column having the heading card "I Really Am Not {2}"; and
 (j) asking the client individual "How do the adjective words on the remaining cards in the "I Am Most of the Time {8}" column apply to the pattern of your behavior, and is that behavior pattern productive?".

9. A method of interactive psycho/social evaluation of a client individual by a therapist according to claim 8 wherein, the five separate column heading cards are arranged in the order: "I Really Am Not {2}"; "I Am Not Most of the Time {8}"; "I Do Not Know If I Am or Not {11}"; "I Am Most of the Time {8}"; and "I Really Am {2}".

10. A method of interactive psycho/social evaluation of a client individual by a therapist according to claim 8 wherein, a complementary word for the word "Afraid" is selected from the group consisting of Aware, Compassionate, Confident, Forgiving, Friendly, Helping, Kind, Listening, Open, Optimistic, Supportive, and Trusting;

and wherein, a complementary word for the word "Avoiding" is selected from the group consisting of Aware, Compassionate, Confident, Forgiving, Friendly, Helping, Kind, Laughing, Listening, Open, Optimistic, Supportive, and Trusting;

and wherein, a complementary word for the word "Aware" is selected from the group consisting of Afraid, Avoiding, Critical, Defensive, Dishonest, Distracted, Distrustful, Hateful, Hyper, Impulsive, Inattentive, Insecure, Jealous, Manipulative, Passive, Pessimistic, Revengeful, and Threatened;

and wherein, a complementary word for the word "Compassionate" is selected from the group consisting of Afraid, Avoiding, Critical, Defensive, Dishonest, Distracted, Distrustful, Hateful, Impulsive, Inattentive, Insecure, Jealous, Manipulative, Passive, Pessimistic, Revengeful, and Threatened;

and wherein, a complementary word for the word "Compassionate" is selected from the group consisting of Afraid, Avoiding, Critical, Defensive, Dishonest, Distracted, Distrustful, Hateful, Impulsive, Inattentive, Insecure, Jealous, Manipulative, Passive, Pessimistic, Revengeful, and Threatened;

and wherein, a complementary word for the word "Confident" is selected from the group consisting of Afraid, Avoiding, Critical, Defensive, Dishonest, Distracted, Distrustful, Hateful, Hyper, Impulsive, Inattentive, Insecure, Jealous, Laughing, Manipulative, Passive, Pessimistic, Revengeful, and Threatened;

and wherein, a complementary word for the word "Critical" is selected from the group consisting of Aware, Compassionate, Confident, Forgiving, Friendly, Helping, Kind, Listening, Open, Optimistic, Supportive, and Trusting; and wherein, a complementary word for the word "Defensive" is selected from the group consisting of Aware, Compassionate, Confident, Forgiving, Friendly, Helping, Kind, Listening, Open, Optimistic, Supportive, and Trusting;

and wherein, a complementary word for the word "Dishonest" is selected from the group consisting of Aware, Compassionate, Confident, Forgiving, Friendly, Helping, Kind, Open, Supportive, and Trusting;

and wherein, a complementary word for the word "Distracted" is selected from the group consisting of Aware, Compassionate, Confident, Forgiving, Friendly, Helping, Kind, Listening, Open, Optimistic, Supportive, and Trusting;

and wherein, a complementary word for the word "Distrustful" is selected from the group consisting of Aware, Compassionate, Confident, Forgiving, Friendly, Helping, Kind, Listening, Open, Optimistic, Supportive, and Trusting;

and wherein, a complementary word for the word "Forgiving" is selected from the group consisting of Afraid, Avoiding, Critical, Defensive, Dishonest, Distracted, Distrustful, Hateful, Hyper, Impulsive, Inattentive, Insecure, Jealous, Laughing, Manipulative, Passive, Pessimistic, Revengeful, and Threatened;

and wherein, a complementary word for the word "Friendly" is selected from the group consisting of Afraid, Avoiding, Critical, Defensive, Dishonest, Distracted, Distrustful, Hateful, Hyper, Impulsive, Inattentive, Insecure, Jealous, Manipulative, Passive, Pessimistic, Revengeful, and Threatened; and wherein, a complementary word for the word "Hateful" is selected from the group Aware, Compassionate, Confident, Forgiving, Friendly, Helping, Kind, Listening, Open, Optimistic, Supportive, and Trusting;

and wherein, a complementary word for the word "Helping" is selected from the group consisting of Afraid, Avoiding, Critical, Defensive, Dishonest, Distracted, Distrustful, Hateful, Hyper, Impulsive, Inattentive, Insecure, Jealous, Laughing, Manipulative, Passive, Pessimistic, Revengeful, and Threatened;

and wherein, a complementary word for the word "Hyper" is selected from the group consisting of Aware, Compassionate, Confident, Forgiving, Friendly, Helping, Listening, Open, Optimistic, Passive; Supportive, and Trusting.

11. A method of interactive psycho/social evaluation of a client individual by a therapist according to claim 8 wherein, a complementary word for the word "Impulsive" is selected from the group consisting of Aware, Compassionate, Confident, Forgiving, Friendly, Helping, Kind, Listening, Open, Supportive, and Trusting;

and wherein, a complementary word for the word "Insecure" is selected from the group consisting of Aware, Compassionate, Confident, Forgiving, Friendly, Helping, Kind, Listening, Open, Supportive, and Trusting;

and wherein, a complementary word for the word "Jealous" is selected from the group consisting of Aware, Compassionate, Confident, Forgiving, Friendly, Helping, Kind, Listening, Open, Optirnistic, Supportive, and Trusting;

and wherein, a complementary word for the word "Kind" is selected from the group consisting of Avoiding, Critical, Defensive, Dishonest, Distracted, Distrustful, Hateful, Hyper, Impulsive, Inattentive, Insecure, Jealous, Laughing, Manipulative, Passive, Pessimistic, and Revengeful;

and wherein, a complementary word for the word "Laughing" is selected from the group consisting of Aware, Compassionate, Confident, Forgiving, Friendly, Helping, Kind, Listening, Open, Optimistic, Passive, Supportive, and Trusting;

and wherein, a complementary word for the word "Listening" is selected from the group consisting of Afraid, Avoiding, Critical, Defensive, Dishonest, Distracted, Distrustful, Hateful, Hyper, Impulsive, Inattentive, Insecure, Jealous, Laughing, Manipulative, Passive, Pessimistic, Revengeful, and Threatened;

and wherein, a complementary word for the word "Manipulative" is selected from the group consisting of Aware, Compassionate, Confident, Forgiving, Friendly, Helping, Kind, Listening, Open, Optimistic, Supportive, and Trusting;

and wherein, a complementary word for the word "Open" is selected from the group consisting of Afraid, Avoiding, Critical, Defensive, Dishonest, Distracted, Distrustful, Hateful, Hyper, Impulsive, Inattentive, Insecure, Jealous, Laughing, Manipulative, Passive, Pessimistic, Revengeful, and Threatened;

and wherein, a complementary word for the word "Optimistic" is selected from the group consisting of Avoiding, Critical, Defensive, Distrustful, Hateful, Insecure, Jealous, Manipulative, Pessimistic, Revengeful, and Threatened;

and wherein, a complementary word for the word "Passive" is selected from the group consisting of Aware, Compassionate, Confident, Forgiving, Friendly, Helping, Kind, Listening, Open, Optimistic, Supportive, and Trusting;

and wherein, a complementary word for the word "Pessimistic" is selected from the group consisting of Aware, Compassionate, Confident, Forgiving, Friendly, Helping, Kind, Open, Optimistic, Supportive, and Trusting;

and wherein, a complementary word for the word "Revengeful" is selected from the group consisting of Aware, Compassionate, Confident, Forgiving, Friendly, Helping, Kind, Listening, Open, Optimistic, Supportive, and Trusting;

and wherein, a complementary word for the word "Supportive" is selected from the group consisting of Afraid, Avoiding, Critical, Defensive, Dishonest, Distracted, Distrustful, Hateful, Impulsive, Inattentive, Insecure, Jealous, Manipulative, Passive, Pessimistic, Revengeful, and Threatened;

and wherein, a complementary word for the word "Threatened" is selected from the group consisting of Aware, Compassionate, Confident, Forgiving, Friendly, Helping, Kind, Listening, Open, Optimistic, Supportive, and Trusting;

and wherein, a complementary word for the word "Trusting" is selected from the group consisting of Avoiding, Critical, Defensive, Dishonest, Distracted, Distrustful, Hateful, Inattentive, Insecure, Jealous, Manipulative, Passive, Pessimistic, Revengeful, and Threatened.

* * * * *

UNITED STATES PATENT AND TRADEMARK OFFICE
CERTIFICATE OF CORRECTION

PATENT NO.         : 7,033,181 B1
APPLICATION NO. : 09/877741
DATED              : April 25, 2006
INVENTOR(S)        : Bennett et al.

It is certified that error appears in the above-identified patent and that said Letters Patent is hereby corrected as shown below:

On the cover page, at item (76) Inventors: Please Delete "Richard W. Bennett" and insert therefore, --Richard C. Bennett--;

In column 2, at line 54; Please delete the number "5";

In claim 8, at column 25, line 34; Please delete "{ }" and insert therefore, --{11}--.

Signed and Sealed this

Eleventh Day of July, 2006

JON W. DUDAS
*Director of the United States Patent and Trademark Office*